(12) United States Patent
Prashant et al.

(10) Patent No.: US 10,414,764 B2
(45) Date of Patent: Sep. 17, 2019

(54) SUBSTANTIALLY PURE VEMURAFENIB AND ITS SALTS

(71) Applicant: SHILPA MEDICARE LIMITED, Raichur, Karnataka (IN)

(72) Inventors: Purohit Prashant, Raichur (IN); Nagnnath Kokare, Raichur (IN); Veera Reddy Yenireddy, Raichur (IN); Chaturvedi Akshay Kant, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 0 days.

(21) Appl. No.: 15/527,721

(22) PCT Filed: Nov. 19, 2015

(86) PCT No.: PCT/IB2015/058964
§ 371 (c)(1),
(2) Date: May 18, 2017

(87) PCT Pub. No.: WO2016/083956
PCT Pub. Date: Jun. 2, 2016

(65) Prior Publication Data
US 2017/0320872 A1 Nov. 9, 2017

(30) Foreign Application Priority Data

Nov. 29, 2014 (IN) .......................... 5990/CHE/2014
Dec. 3, 2014 (IN) .......................... 6087/CHE/2014

(51) Int. Cl.
| C07D 401/10 | (2006.01) |
| C07D 401/14 | (2006.01) |
| C07D 401/02 | (2006.01) |
| A61K 31/437 | (2006.01) |
| A61K 31/4353 | (2006.01) |
| C07D 471/04 | (2006.01) |

(52) U.S. Cl.
CPC ........ C07D 471/04 (2013.01); C07B 2200/13 (2013.01)

(58) Field of Classification Search
CPC .. C07D 401/02; C07D 401/10; C07D 401/14; A61K 31/437; A61K 31/4353
USPC .......................... 546/119, 121; 514/300, 303
See application file for complete search history.

(56) References Cited

U.S. PATENT DOCUMENTS

| 7,504,509 B2 | 3/2009 | Ibrahim et al. |
| 7,863,288 B2 | 1/2011 | Ibrahim et al. |
| 8,143,271 B2 | 3/2012 | Ibrahim et al. |
| 8,329,724 B2 | 12/2012 | Hildbrand et al. |
| 8,530,661 B2 | 9/2013 | Hildbrand et al. |
| 8,741,920 B2 | 6/2014 | Hildbrand et al. |
| 8,865,735 B2 | 10/2014 | Ibrahim et al. |
| 9,663,517 B2 * | 5/2017 | Desai .................... C07D 471/04 |
| 2010/0310659 A1 | 12/2010 | Desai et al. |
| 2014/0094611 A1 | 4/2014 | Ibrahim |

FOREIGN PATENT DOCUMENTS

| WO | 2007002325 A1 | 1/2007 |
| WO | 2014008270 A1 | 1/2014 |
| WO | 2014159353 A1 | 10/2014 |

* cited by examiner

Primary Examiner — Niloofar Rahmani

(57) ABSTRACT

The present invention relates to a process for the preparation substantially pure propane-1-sulfonicacid-{3-[5-(4-chlorophenyl)-1H-pyrrolo[2,3-b]pyridine-3-carbonyl]-2,4-difluoro-phenyl}-amide or Vemurafenib of Formula (I).

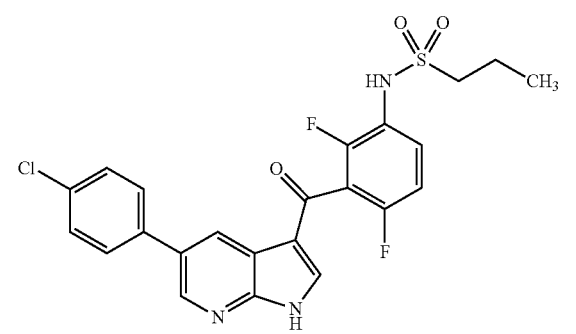

The present invention further relates to a process for the preparation substantially pure propane-1-sulfonic acid-{3-[5-(4-chlorophenyl)-1H-pyrrolo[2,3-b]pyridine-3-carbonyl]-2,4-difluoro-phenyl}-amide trifluoro methane sulfonic acid salt or Vemurafenib triflate of Formula (VII)

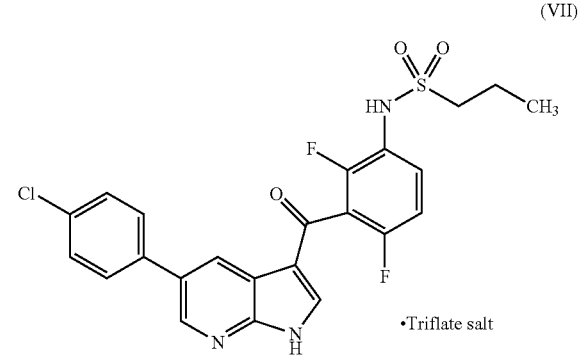

3 Claims, 2 Drawing Sheets

SUBSTANTIALLY PURE VEMURAFENIB AND ITS SALTS

FIELD OF THE INVENTION

The present invention relates to a process for the preparation substantially pure propane-1-sulfonicacid-{3-[5-(4-chlorophenyl)-1H-pyrrolo[2,3-b]pyridine-3-carbonyl]-2,4-difluoro-phenyl}-amide or Vemurafenib of Formula (I) and its trifluomethane sulfonic acid salt (may also called as triflate salt) of Formula VII

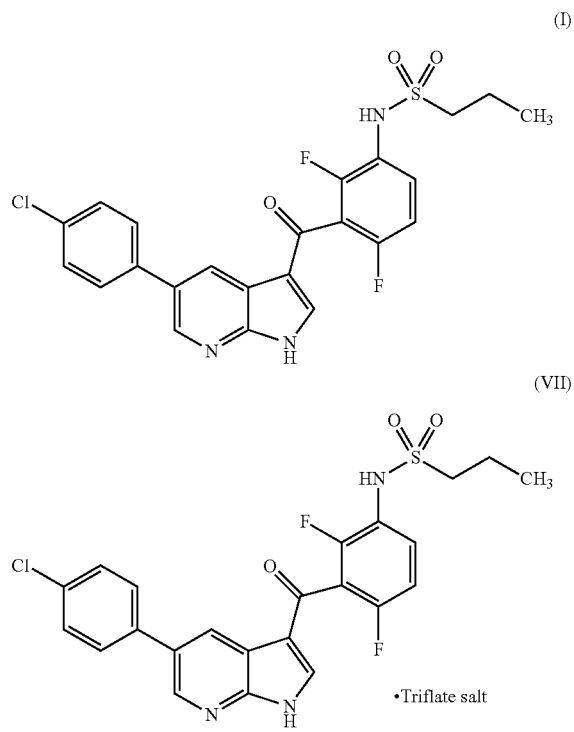

BACKGROUND OF THE INVENTION

Propane-1-sulfonicacid-{3-[5-(4-chlorophenyl)-1H-pyrrolo[2,3-b]pyridine-3-carbonyl]-2,4-difluoro-phenyl}-amide or Vemurafenibis a low molecular weight, orally available, inhibitor of some mutated forms of BRAF serine-threonine kinase, including BRAF. Vemurafenib also inhibits other kinases in vitro such as CRAF, ARAF, wild-type BRAF, SRMS, ACK1, MAP4K5 and FGR at similar concentrations. Some mutations in the BRAF gene including V600E result in constitutively activated BRAF proteins, which can cause cell proliferation in the absence of growth factors that would normally be required for proliferation. Vemurafenib has anti-tumor effects in cellular and animal models of melanomas with mutated BRAF.

Vemurafenib was approved by USFDA in 2011 and is marketed under the brand name Zelboraf®, has been shown to cause programmed cell death in melanoma cell lines. Vemurafenib interrupts the B-Raf/MEK step on the B-Raf/MEK/ERK pathway—if the B-Raf has the common V600E mutation.

Vemurafenib only works in melanoma patients whose cancer has a V600E BRAF mutation (that is, at amino acid position number 600 on the B-Raf protein, the normal valine is replaced by glutamic acid). About 60% of melanomas have this mutation. It also has efficacy against the rarer BRAF V600K mutation. Melanoma cells without these mutations are not inhibited by Vemurafenib; the drug paradoxically stimulates normal BRAF and may promote tumor growth in such cases Vemurafenib is chemically known as propane-1-sulfonic acid-{3-[5-(4-chlorophenyl)-1H-pyrrolo[2,3-b]pyridine-3-carbonyl]-2,4-difluoro-phenyl}-amide(I). Vemurafenib is a white to off-white crystalline solid with the empirical formula $C_{23}H_{18}ClF_2N_3O_3S$ and a molecular weight of 489.99. It is practically insoluble in aqueous media.

As per the Chemistry review available in Drugs@FDA for Vemurafenib. Drugs substance contain "Five impurities are specified at levels exceeding this applicable qualification threshold because they have been detected in DS batches in amounts that exceeded the qualification threshold Data from appropriate toxicology studies are provided to qualify the proposed limits. Thirty four development or pilot scale batches and eight commercial scale batches have been reported. Specifications and analytical methods have been established to adequately control the identity, quality, purity and stability of the drug substance."

Further, as per the Pharmacology review available in Drugs@FDA for Vemurafenib "A single impurity was identified during the course of the review as being above the level for qualification. The specification for this impurity is . . . % and it was qualified in the 13-week dog study. Other impurities discussed with the chemistry review team did not exceed the 0.15% level described in the ICH Q3A(R2) guidance and, therefore, did not require qualification in animal studies."

As per the scientific discussion "Vemurafenib can exist as several polymorphs and solvates. The crystalline Form II is thermodynamically the most stable. Crystalline Vemurafenib (Form II) is a white to almost white non-hygroscopic powder with a melting point of about 271° C. Its solubility in water is very low (<0.0001 mg/ml) and it is not appreciably soluble in many common organic solvents either. When processed with HPMC-AS, Vemurafenib becomes an amorphous white to almost white powder which is slightly hygroscopic. The product with (HPMC-AS) is non-crystalline."

From the above citations it is abundantly clear that Vemurafenib marketed in the form of crystalline Form II, contains inherently a known impurity, which is exceeding the requirement of ICH guidelines, which was subsequently attempted to get qualified in the 13-week dog study. In view of the aforementioned disclosures, there appears to be a need for development of substantially pure Vemurafenib, which meets the requirements of ICH guidelines from impurities perspective besides maintaining the stability for longer durations.

Vemurafenib is generically disclosed in U.S. Pat. No. 7,504,509, however, there is no specific disclosure of the structure in this patent. Vemurafenib is specifically disclosed in U.S. Pat. No. 7,863,288 and more specifically U.S. Pat. No. 8,143,271.

Disclosures of US patent '288 and US '271 both disclose same process for the preparation of Vemurafenib. The process disclosed specifically for the preparation of Vemurafenib is delineated below:

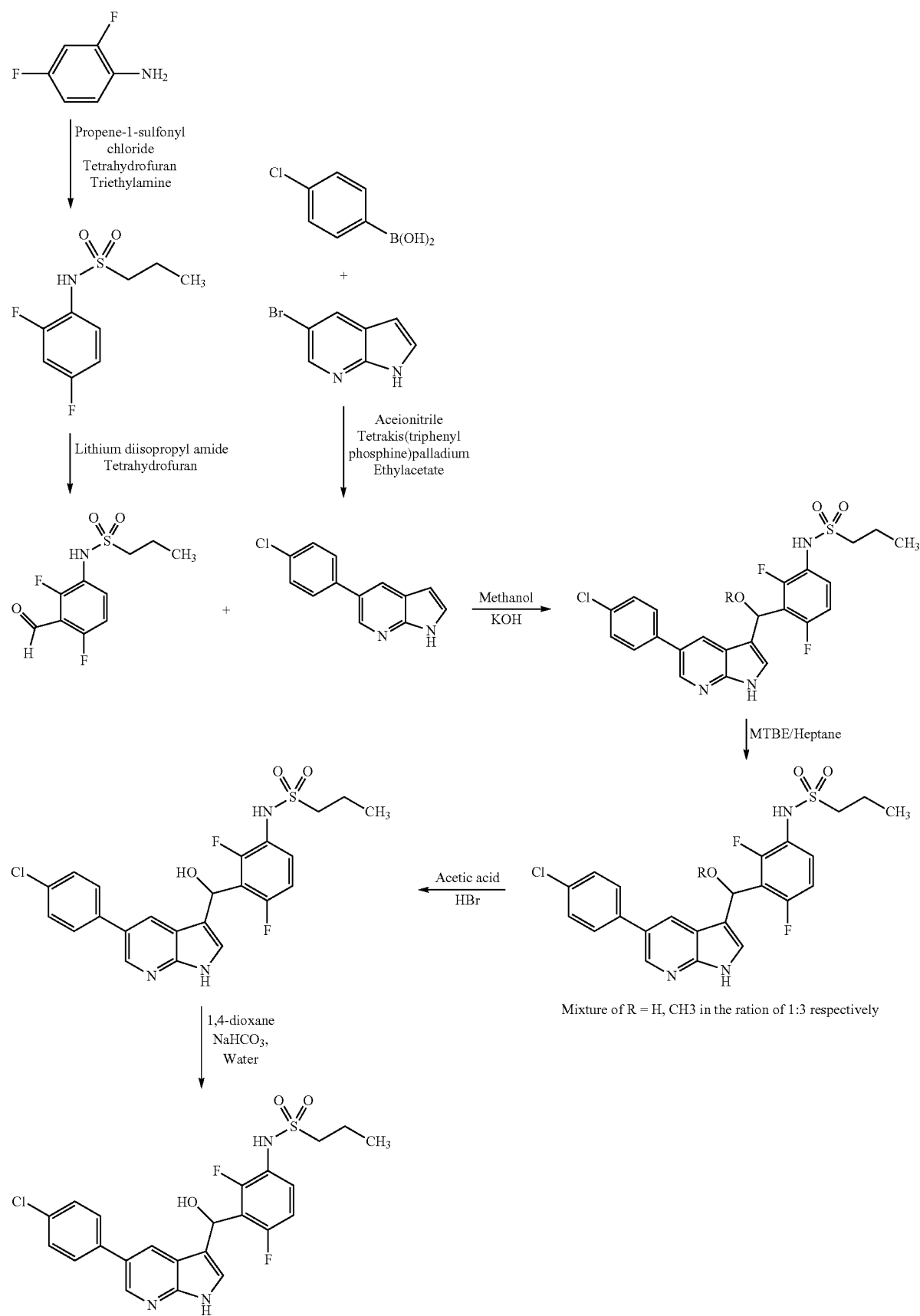

These patents do not provide and insight about the impurity concern as well as disclosure of any purity of the final product. However, it is clear from Drugs@FDA that the product obtained as per the process is exceeding in the levels of impurity than the applicable qualification i.e., exceeding 0.15% level as described in the ICH Q3A. In view of this it is necessary to develop a process resulting in the product, which is complying with the ICH requirements of quality parameters.

U.S. Pat. No. 8,741,920 and its corresponding equivalents U.S. Pat. No. 8,329,724 and U.S. Pat. No. 8,530,661 discloses a different process for the preparation of Vemurafenib. The process is as disclosed below:

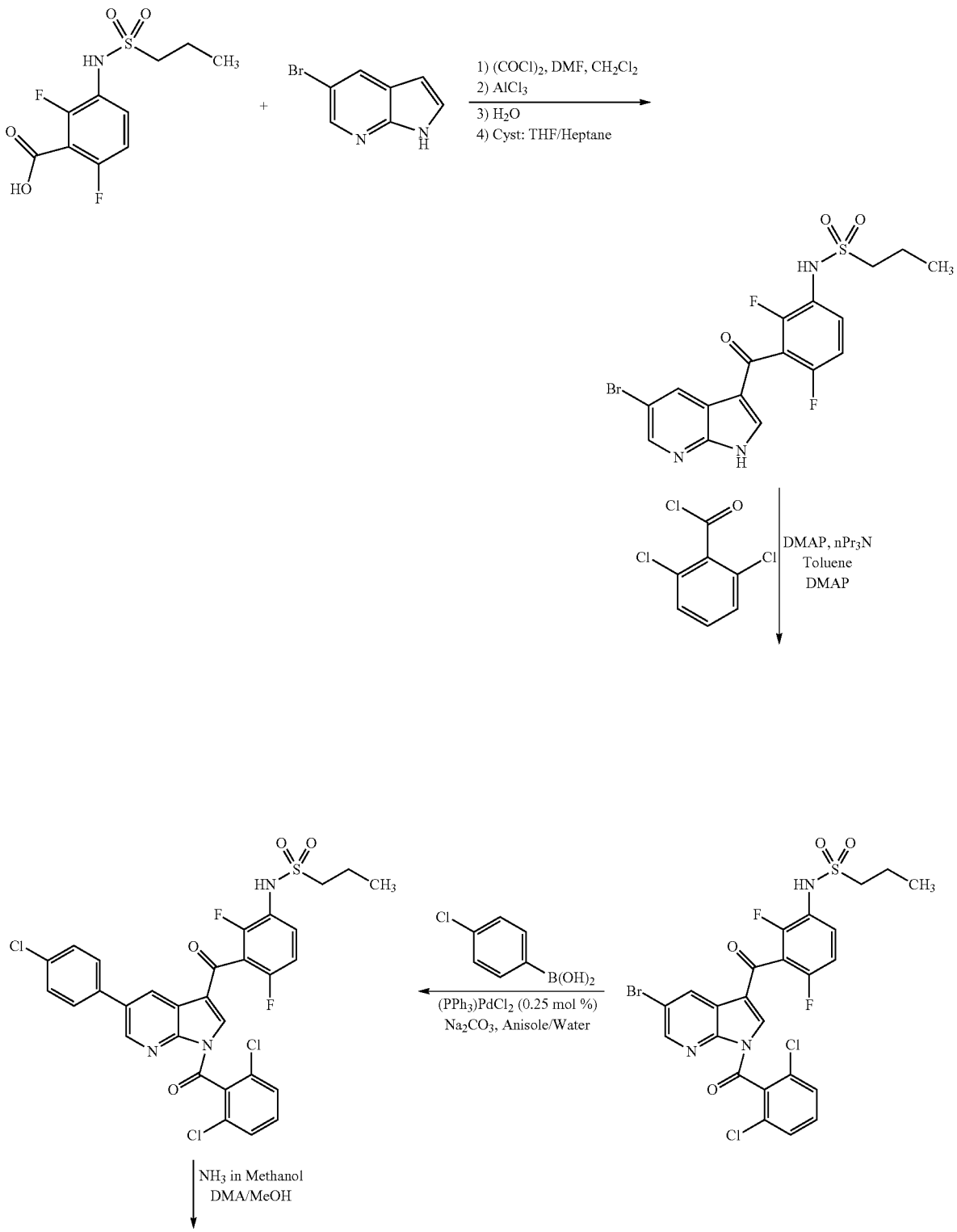

-continued

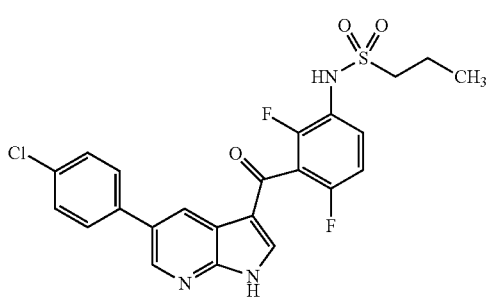

These patents further disclosed two compounds A and B, which are by-products for the route of synthesis disclosed in these patents Compound A

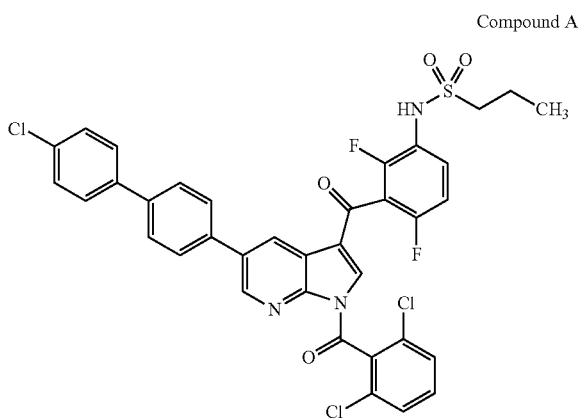

Compound B

These patents have not disclosed any generalized impurities formed during the process development. Further, these patents have also not disclosed perfect (real) purity obtained as per this process, these patents broadly mentioned the purity as ≥99% and does not disclosed the content of total impurities formed in the final active pharmaceutical ingredient (API).

Further, it mentions that "the impurity/trace amounts of the compound of formula (B) will not affect the pharmacological or toxicity profile of any potential future medicament or pharmaceutical preparation containing Vemurafenib, said compound may serve only as a way of detecting the apparent process has been used to manufacture the Vemurafenib"

A reproduction of an earlier patent process U.S. Pat. No. 7,863,288 though indicates the presence of said compound, however materially questions as to how it serves any purpose/merit in US '920.

Inventors of the present application during extensive evaluation observed that such compound of Formula (B) may be more often formed from the key starting material (4-chlorophenyl boronic acid), which is also known to be used earlier process disclosed in US '288. In the process of purification according to the present invention, it results in providing a highly pure/substantially pure Vemurafenib, which may also be devoid of such compound of formula (B) with exceeding purity of >99.5% (By HPLC).

Inventors also observed that such compound of formula (B) formation may also be avoided if the key starting material (4-chlorophenyl boronic acid) is purified prior to any condensation reaction under modest conditions. This also serves as an embodiment according to the present invention.

Prabha. N. Ibrahim et al. in U.S. Pat. No. 8,865,735 disclosed a solid form of Vemurafenib, wherein said solid form is selected from the group consisting of a) a substantially amorphous form of compound 1 selected from form XXIV, XXV, XXVI or combinations thereof, wherein the compound 1 is molecularly dispersed;

b) a solvate selected from form III, IV, V, VI, VII, IX, X, XI, XII, XIII, XIV or XV;

c) a polymorph selected from form VIII or XVI; and d) the sulfuric acid-, hydrobromic acid- or hydrochloric acid salt of Vemurafenib.

Further, this patent discloses that the amorphous form of Vemurafenib is preferentially substantially pure, meaning the amorphous form includes less than 0.1% by weight of impurities, including other polymorph forms of Vemurafenib. At least about 30-99.9% by weight of the total of Vemurafenib in the composition is present as the amorphous form. This patent not disclosed any generalized impurities formed during the process development and not disclosed the purity obtained as per this process. This patent mentioned the amorphous Vemurafenib obtained as per the process has a polymorphic purity of at least about 99.9% by weight.

Prabha. N. Ibrahim et al. in US 2014/0094611 disclosed a process for the preparation of Vemurafenib. The process disclosed is as summarized below:

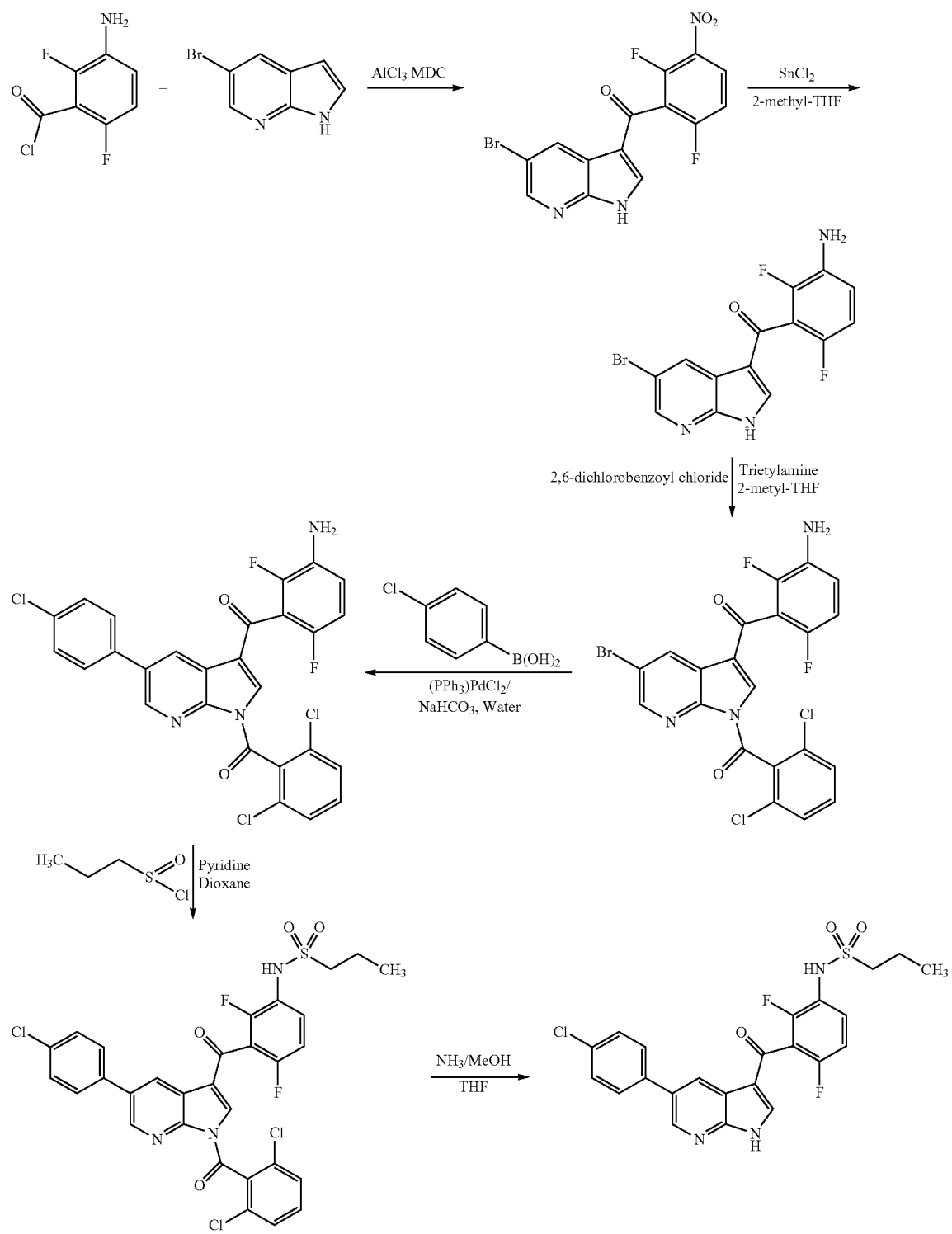

Dipen Desai et al. in US2010/0310659 disclosed different crystalline forms like crystalline Form-1, crystalline Form-2, mesylate salt, tosylate salt, maleate salt, oxalate salt and dichloro acetate salt of Vemurafenib. This patent publication has also not disclosed the purity of the products obtained as per this patent publication. Further, as it is quite clear from EMEA and Drugs @FDA that the marketed form is Form-II that contains a known impurity, which is exceeding the requirement of ICH guidelines. This patent publication further discloses pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylene diamine, meglumine, hydroxyl ethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine.

Frank Lehmann et al. in WO 2014/008270 discloses Choline salt and esylate salt of Vemurafenib. This patent also disclosed N-methyl Vemurafenib and crystalline T-1 form of Vemurafenib. The maximum purity disclosed for Choline salt is 99.4%. WO '270 not disclosed any purity of esylate salt of Vemurafenib. WO '270 also disclosed the purity of N-methyl Vemurafenib as 96.89%.

Wolfgang Albrecht in WO 2014/159353 discloses Hydrochloride salt of Vemurafenib. This patent publication not disclosed any purity for Vemurafenib hydrochloride obtained as per the patented process. The process disclosed in this patent publication involves stirring over night to form the hydrochloride salt, which is cumbersome and longtime stirring may leads to the formation of process related impurities. Further, the present inventors repeated the process and the purity obtained by HPLC analyzed and found to be 98.13.

In view of the above it is pertinent to note that there is a need to develop new salt forms of Vemurafenib as well as free base of Vemurafenib having further improved physical and/or chemical properties besides high purity levels. Hence it was thought worthwhile by the inventors of the present application to explore novel pharmaceutically acceptable salts of Vemurafenib, which may further improve the characteristics of drug Vemurafenib and in developing the substantially pure Vemurafenib. Low aqueous solubility is the major problem encountered with formulation development.

As polymorphism has been given importance in the recent literatures owing to its relevance to the drugs having oral dosage forms due to its apparent relation to dose preparation/suitability in composition steps/bioavailability and other pharmaceutical profiles, stable polymorphic form of a drug has often remained the clear choice in compositions due to various reasons of handling, mixing and further processing including bioavailability and stability.

Exploring new process for developing a stable and pure form of Vemurafenib salts, which are amenable to scale up for pharmaceutically active/useful compounds such as Vemurafenib triflate in the preparation of Vemurafenib free base may thus provide an opportunity to improve the drug performance characteristics of products such as purity and solubility. Hence, inventors of the present application report a process for the preparation of a stable and substantially pure form of propane-1-sulfonic acid-{3-[5-(4-chlorophenyl)-1H-pyrrolo[2,3-b]pyridine-3-carbonyl]-2,4-difluoro-phenyl}-amide or Vemurafenib, which may be industrially amenable and usable for preparing the corresponding pharmaceutical compositions.

The present invention provides an improved process for the preparation of substantially pure propane-1-sulfonic acid-{3-[5-(4-chlorophenyl)-1H-pyrrolo[2,3-b]pyridine-3-carbonyl]-2,4-difluoro-phenyl}-amide or Vemurafenib, wherein substantially pure material having a purity of greater than 99.5% by HPLC, which is not reported earlier in the prior art and meeting the quality of ICH guidelines. Vemurafenib obtained by the process of the present invention is non-hygroscopic and chemically stable and has good dissolution properties.

In view of the above and to overcome the prior-art problems the present inventors had now developed an improved process for the preparation of substantially pure Vemurafenib, using industrially feasible and viable process, with the use of industrially friendly solvents, which does not include tedious work up and time lagging steps.

OBJECTIVE OF THE INVENTION

The main objective of the invention relates to a process for the preparation of substantially pure Vemurafenib.

Yet another objective of the invention relates to a process for the preparation of substantially pure Vemurafenib, wherein Vemurafenib obtained is having a purity of greater than 99.5% and water solubility of greater than 0.001 mg/ml.

Yet another aspect of the invention relates to a process for the preparation of substantially pure Vemurafenib, wherein substantially pure Vemurafenib contains the process related impurities A, B, C, D and E collectively below 0.3% and meeting the ICH guidelines.

Yet another aspect of the invention relates a substantially pure crystalline Vemurafenib having purity greater than 99.5%

Yet another objective of the invention relates to substantially pure Vemurafenib trifluoro methane sulfonic acid salt and its process for the preparation thereof, wherein Vemurafenib trifluoro methane sulfonic acid salt obtained is having a purity of greater than 99.5% and water solubility of greater than 0.001 mg/ml.

Yet another aspect of the invention relates to a process for the preparation of substantially pure Vemurafenib trifluoro methane sulfonic acid salt, wherein substantially pure Vemurafenib trifluoro methane sulfonic acid salt contains the process related impurities A, B, C, D and E collectively below 0.3% and meeting the ICH guidelines.

SUMMARY OF THE INVENTION

The present invention relates to a process for the preparation of substantially pure Vemurafenib of Formula (I)

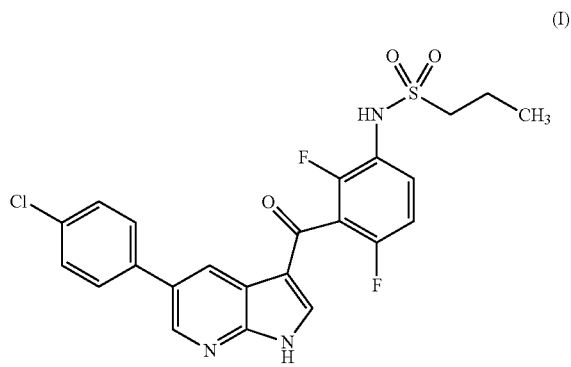 [SMILES: CCCS(=O)(=O)Nc1ccc(F)c(C(=O)c2c[nH]c3ncc(-c4ccc(Cl)cc4)cc23)c1F]

comprising the steps of—
a) reacting 2, 6-difluoro-3-(((propan-1-yl) sulphonyl) amino) benzoic acid (II) with a halogenating agent in the ratio between 2-10 v/w times, to provide a compound of Formula (III);

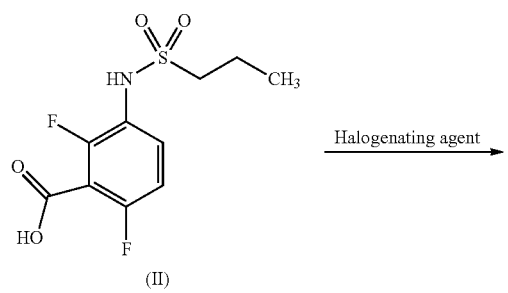

(II)

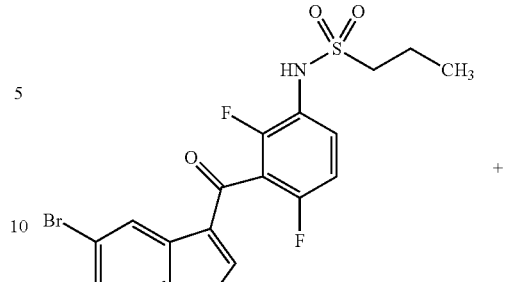

(V)

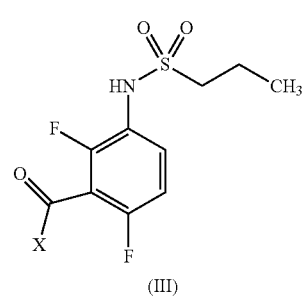

(III)

b) reacting compound of Formula (III) with 5-bromo-1H-pyrrolo[2,3-b]pyridine (IV) to provide a compound of Formula (V)

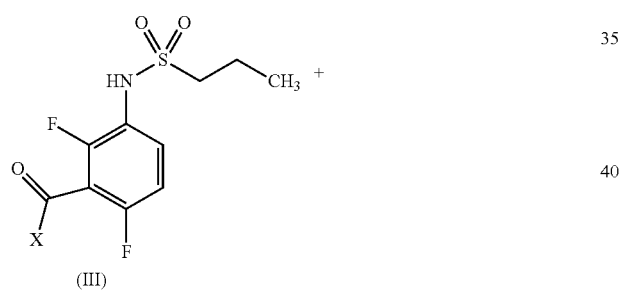

(III)

(IV)

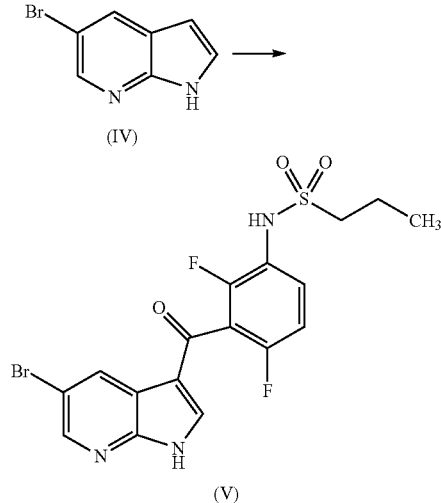

(V)

c) reacting compound of Formula (V) with 4-Chlorophenylboronic acid (VI) to form Vemurafenib(I);

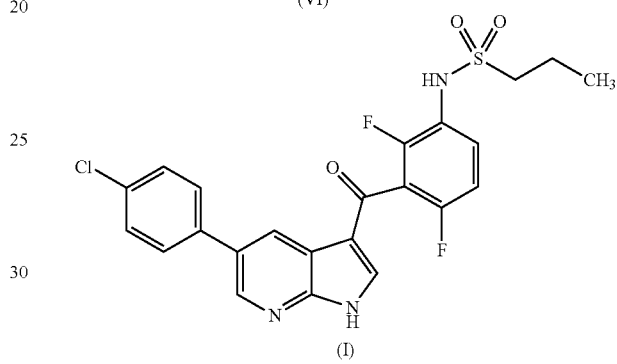

(VI)

(I)

d) optionally purifying Vemurafenib using alkaline solution;

e) reacting Vemurafenib obtained in step (C) with trifluoro methane sulfonic acid salt to provide Vemurafenib trifluoromethane sulfonic acid salt(VII);

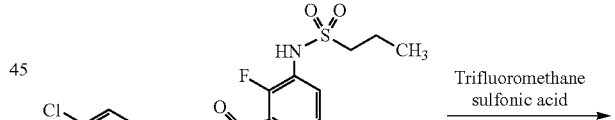

(I)

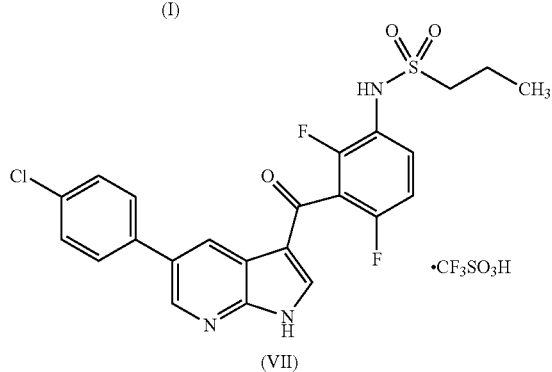

(VII)

f) treating compound of Formula (VII) with an alkaline solution to obtain substantially pure Vemurafenib(I) having a purity of greater than 99.5%; and/or

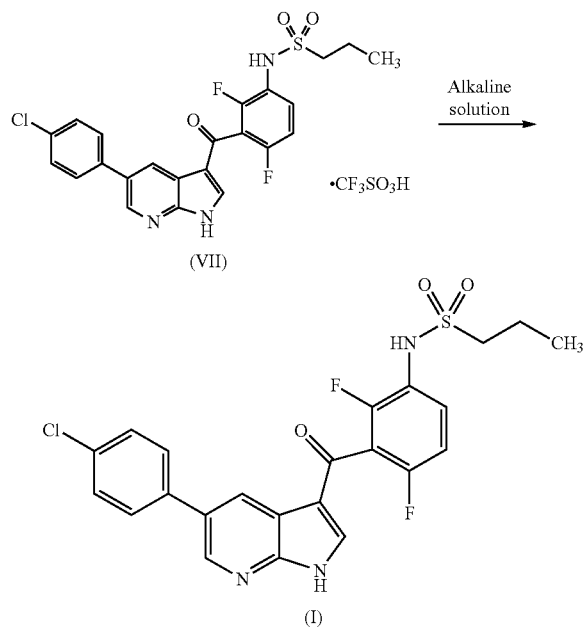

g) optionally, repeating the steps d) and e) to get the desired purity.

Another aspect of the present invention relates to a process for the preparation of substantially pure Vemurafenib comprising the steps of—
a) treating Vemurafenib or Vemurafenib hydrate or solvate or salt with an alkaline solution; and
b) optionally, reacting Vemurafenib or Vemurafenib hydrate or solvate or salt with an acid forming salt to form the corresponding salt, followed by basification with an alkaline solution to obtain substantially pure Vemurafenib(I).

Yet another aspect the present invention relates to substantially pure Vemurafenib having a purity of greater than 99.5% and water solubility of greater than 0.001 mg/ml.

Yet another aspect of the present invention relates to substantially pure Vemurafenib having a purity of greater than 99.5%, wherein process related impurities A, B, C, D and E are collectively below 0.3% and meeting the ICH guidelines.

Yet another aspect of the present invention relates to a substantially pure crystalline Vemurafenib having a purity of greater than 99.5%.

Another aspect of the present invention relates to a process for the preparation of substantially pure Vemurafenib trifluoro methane sulfonic acid salt comprising the steps of—
a) treating Vemurafenib (I) or Vemurafenib hydrate or solvate or salt with trifluoro methane sulfonic acid salt to obtain substantially pure Vemurafenib trifluoro methane sulfonic acid salt (VII); and
b) optionally, basifying followed by repeating the steps a) to get the desired purity.

Yet another aspect the present invention relates to substantially pure Vemurafenib trifluoro methane sulfonic acid salt having a purity of greater than 99.5% and water solubility of greater than or equal to (hereinafter refer as ≥) 0.001 mg/ml.

Yet another aspect of the present invention relates to substantially pure Vemurafenib trifluoro methane sulfonic acid salt having a purity of greater than 99.5% wherein process related impurities A, B, C, D and E are collectively below 0.3%.

DETAILED DESCRIPTION OF THE INVENTION

Figure 1:
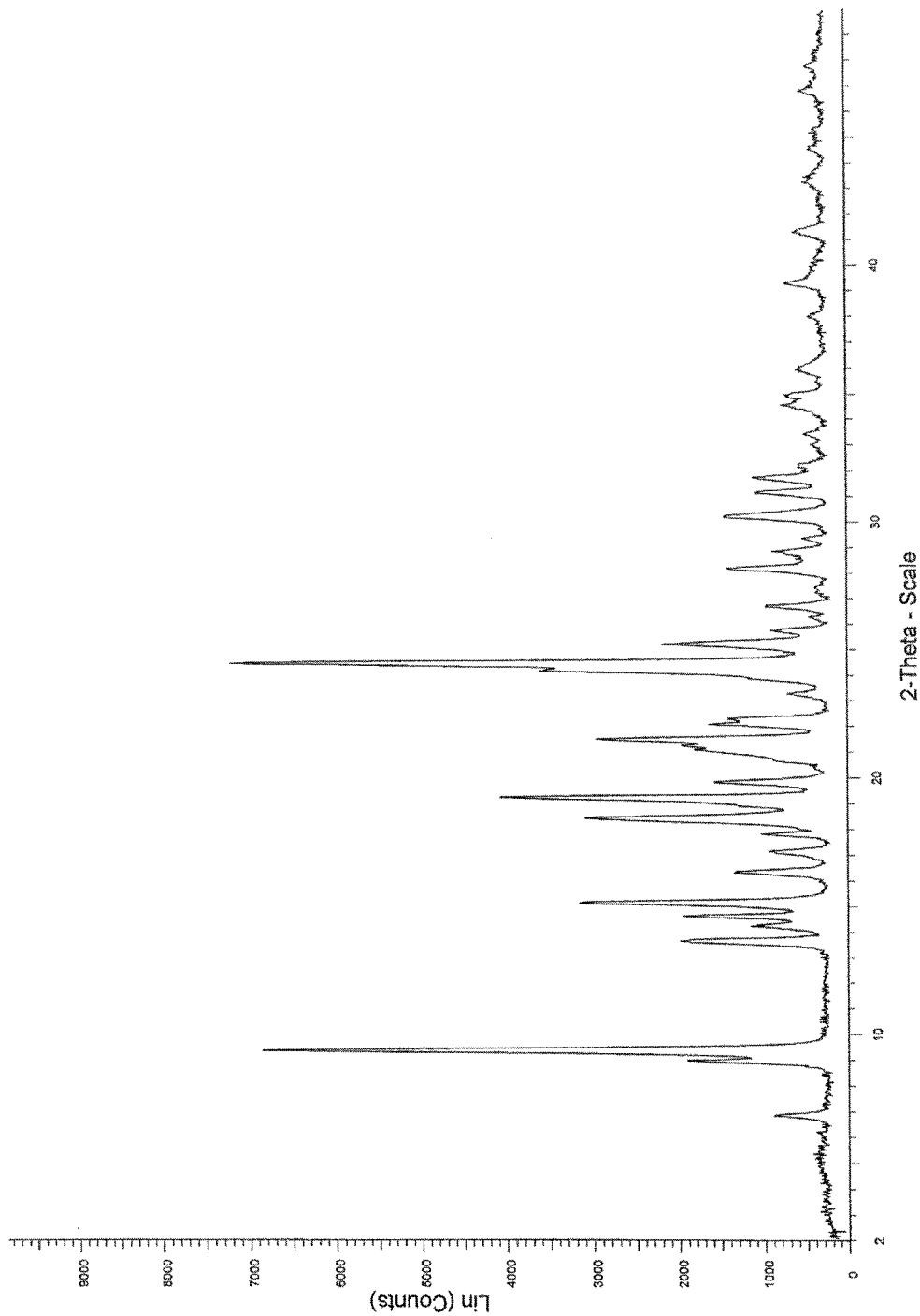
FIG. 1 is an example of X-ray powder diffraction ("XRPD") pattern of crystalline Vemurafenib (I) obtained according to example-5 of the present invention.
Figure 2:
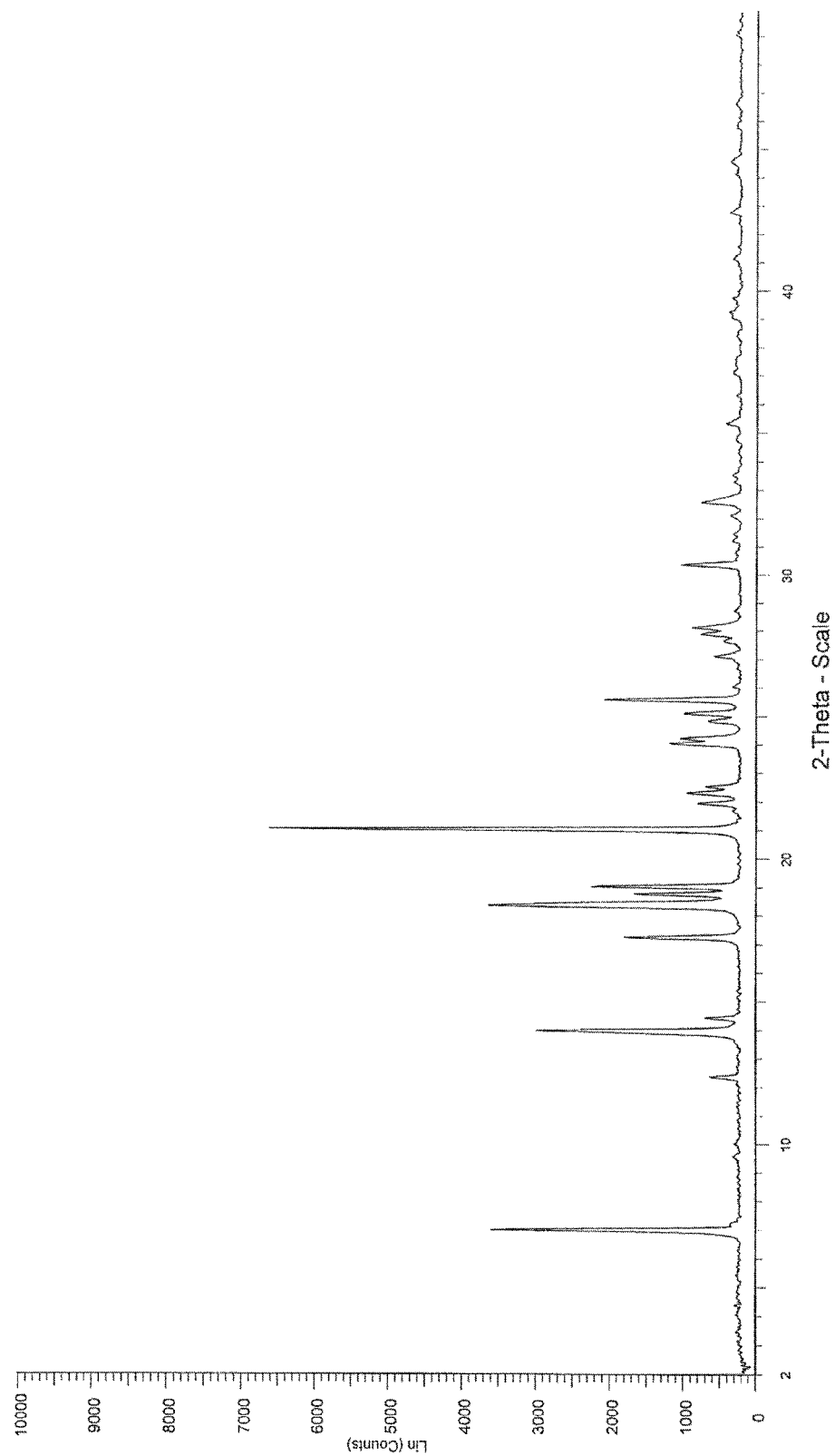
FIG. 2 is an example of X-ray powder diffraction ("XRPD") pattern of crystalline Vemurafenib Triflate (I) obtained according to example-6 of the present invention.

The present invention relates to a process for the preparation of substantially pure Vemurafenib of Formula (I) comprising the steps of reacting 2, 6-difluoro-3-(((propan-1-yl) sulphonyl) amino) benzoic acid (II) with a halogenating agent selected from thionyl chloride, oxalyl chloride, Phosphorous trichloride, Phosphorous pentachloride, Phosphorous oxy chloride; in the ratio between 2-10 v/w times of 2, 6-difluoro-3-(((propan-1-yl) sulphonyl) amino) benzoic acid (II); using a solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof; at a temperature ranging from 50-140° C.; which is further distilled off to obtain a semi solid material of Formula (III).

The use of halogenating reagents in a ratio of between 2-10 v/w times with respect to 2, 6-difluoro-3-(((propan-1-yl) sulphonyl) amino) benzoic acid (II) leads the reaction, which is free of process related impurities like excess halogenated materials.

The prior art publications discloses a use of halogenating agents in a ratio of above 10 v/w, which leads to the formation of process related impurities, and is carried out for further steps results in the formation of Vemurafenib having the corresponding excessively halogenated impurities. The Vemurafenib obtained as per the prior-art process does not meet the requirements of ICH guidelines.

The obtained semi solid material of Formula (III) reacted with 5-bromo-1H-pyrrolo[2,3-b]pyridine (IV) of to provide a compound of Formula (V); in presence of Lewis acid selected from Aluminum chloride, Aluminum bromide, Boron trichloride, Boron trifluoride, Boron complexes, Tin chloride, Iron bromide, Iron chloride; using a solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof; at a temperature ranging from 20-25° C. for 13 to 15 hours. Water was added slowly to the obtained reaction mass to precipitate the product, filtered the material and washed with water. The obtained wet cake is purified till the desired purity was obtained. The obtained wet cake is washed with organic solvent and washed twice with water. The organic layer was dried over sodium sulphate and distilled off completely to get residue. To the residue organic solvent was added and stirred for 45 min to 1 hr. Precipitated product was filtered, washed with organic solvent and dried at 50-55° C. still constant weight appears to yield a compound of Formula (V).

The obtained compound of Formula (V) is reacted with 4-Chlorophenylboronic acid (VI) using a solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof; in presence of potassium or sodium carbonate and Bis (triphenylphosphine) palladium (II) dichloride,tetrakistriphenyl phosphine, palladium acetate; at a temperature ranging from 70-120° C. for 4 hrs to 12 hrs. Water was added and the collected aqueous layer was extracted twice using an organic solvent. The combined organic layer was washed with water and dried over sodium sulfate. The dried organic layer was purified, precipitated and dried to yield Vemurafenib.

In another embodiment of the present invention relates to purification of Vemurafenib. The Vemurafenib of the compound of the formula (I) obtained from the above stage may be purified by treating the compound of the formula (I) or a reaction mixture or a solvated form thereof with an "alkaline solution".

The "alkaline solution" utilized in this step comprising a base selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate and a medium derived from water or a miscible organic solvent.

The strength of alkaline solution used is usually variable between 0.5N to 2.0 N and is prepared using the base in water or a miscible organic solvent at a temperature ranging from 25-30° C., followed by stirring the reaction mass for 30 min to get clear solution.

In a particular embodiment, such alkaline solution was utilized as aqueous based sodium hydroxide having strength about 1 N.

To the subsequent reaction mass mixture, ethyl acetate and toluene was added at 25-30° C., stirred the contents for 10 min and separated the aqueous layer. To the Aqueous layer mixture ethyl acetate and toluene was added under stirring and maintained stirring at 25-30° C. for 30-60 min to get product precipitation. Precipitated product was filtered on Buchner funnel and washed with water to get wet cake material. The wet cake material was slurred in 5% ammonium chloride solution and filter on Buchner funnel, washed with water and suck dried for 30 min. The wet cake material is unloaded and dried under vacuum at 70-75° C. for about 6 hours to yield pure titled product.

In another embodiment of the present invention relates to purification of Vemurafenib. The Vemurafenib of the compound of the formula (I) obtained from the above stage may be purified by treating the compound of the formula (I) or a reaction mixture or a solvated form thereof is treated with an acid selected from trifluoromethanesulphonic acid, difluoromethanesulphonic acid, dichloroacetic acid, glucornic acid, gluconic acid, Ferulate, glycols and glycol ethers; to form a salt of the compound of the formula (I) which precipitates from the solution containing the solved compound of the formula (I), the salt of the compound of the formula (I) is then treated with an aqueous basic solution to precipitate the pure form of compound of the formula (I), preferably at a temperature of from 15° C. to 45° C., most preferably from 25° C. to 35° C. If required, repeat again the acidification followed by basification to obtained desired purity, which is greater than 99.5%.

The Vemurafenib of the compound of the formula (I) is dissolved in a solvent selected from solvent selected from alcohol (C1-3) or Ketones (C3-6) or organic solvents (C1-8 alkanes, dimethyl formamide) or halogenated organic solvents (Methylene dichloride, Ethylene dichloride) or Ethers (Methyl tertiary butyl ether, tetrahydrofuran) or sulphoxides (dimethyl sulphoxide) or esters (Ethyl acetate, benzyl acetate, isoamyl acetate) or water or mixtures thereof. To the obtained solution acid was added; preferably Trifluoro methane sulphonic acid at a temperature ranging from −10 to 30° C. for 30 min to 2 hrs to yield wet product, which was dried under vacuum at 50-55° C. for 2 hrs to yield Vemurafenib-triflic acid salt.

The obtained pure Vemurafenib trifluoro methane sulfonic acid salt was analyzed, if it is not matching with the desired purity; again repeat the process by treating the Vemurafenib trifluoro methane sulfonic acid salt with an alkali solution, followed by saltification using trifluoro methane sulfonic acid salt to obtain substantially pure Vemurafenib trifluoro methane sulfonic acid salt having a purity of greater than 99.5% and meeting the ICH guidelines.

Another embodiment of the invention relates to a process for the preparation of substantially pure Vemurafenib trifluoro methane sulfonic acid salt, wherein Vemurafenib trifluoro methane sulfonic acid salt obtained is having a purity of greater than 99.5% and water solubility of ≥0.001 mg/ml.

Yet another embodiment of the invention relates to a process for the preparation of substantially pure Vemurafenib or its trifluoro methane sulfonic acid salt having a purity of greater than 99.6%.

Yet another embodiment of the invention relates to a process for the preparation of substantially pure Vemurafenib or its trifluoro methane sulfonic acid salt having a purity of greater than 99.7%.

Yet another embodiment of the invention relates to a process for the preparation of substantially pure Vemurafenib or its trifluoro methane sulfonic acid salt having a purity of greater than 99.8%.

Another embodiment of the present invention related to a process for the preparation of substantially pure Vemurafenib trifluoro methane sulfonic acid salt comprising the steps of
  a) treating Vemurafenib(I) or Vemurafenib hydrate or solvate or salt with trifluoro methane sulfonic acid salt to obtain substantially pure Vemurafenib trifluoro methane sulfonic acid salt (VII); and
  b) optionally, basifying followed by repeating the steps a) to get the desired purity.

The obtained Vemurafenib triflic acid salt is dissolved in a solvent selected from solvent selected from alcohol (C1-4) or Ketones (C3-6) or organic solvents (C1-8 alkanes, dimethyl formamide, toluene, xylene) or halogenated organic solvents (Methylene dichloride, Ethylene dichloride) or Ethers (Methyl tertiary butyl ether, tetrahydrofuran, Di-isopropyl ether) or sulphoxides (dimethyl sulphoxide) or esters (Ethyl acetate, benzyl acetate, isoamyl acetate) or water or mixtures thereof at a temperature ranging from 25-30° C. and stirred for 30 min to get clear solution. The obtained solution was treated with an alkaline solution, wherein alkaline solution used is prepared using a base selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate; in a solvent selected from organic solvent or water. The reaction mass was stirred for 30 min to 4 hrs depending on the acid used. After completion of the reaction, the reaction mass was cooled to a temperature ranging from 0-10° C. and maintained the reaction mass under stirring for 30 min to 4 hrs. The precipitated product was filtered, washed with organic solvent or a mixture of organic solvent or mixture of organic solvent and water to get wet cake, which was dried under vacuum at 50-85° C. for 3 hrs to 6 hrs to yield pure Vemurafenib.

The obtained pure Vemurafenib was analyzed, if it is not matching with the desired purity; again repeat the process by treating the Vemurafenib with acid to prepare the corresponding salt, followed by treating with an alkali solution to obtain substantially pure Vemurafenib having a purity of greater than 99.5% and meeting the ICH guidelines.

Another embodiment of the invention relates to a process for the preparation of substantially pure Vemurafenib according, wherein Vemurafenib obtained is having a purity of greater than 99.5% % and water solubility of greater than 0.001 mg/ml.

In yet another embodiment of the invention related to a process for the preparation of substantially pure Vemurafenib or its salts, wherein substantially pure Vemurafenib contains the process related impurities A, B, C, D and E collectively below 0.3% and meeting the ICH guidelines.

Impurity- A

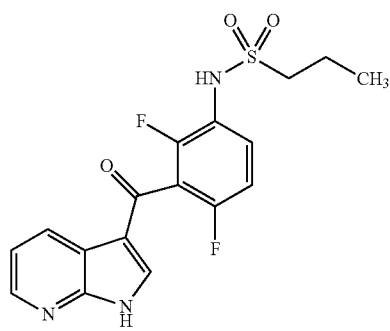

Impurity- B

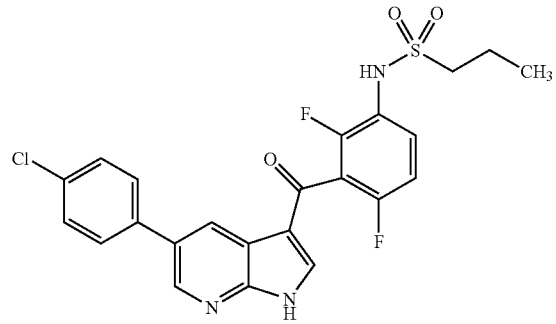

Impurity- C

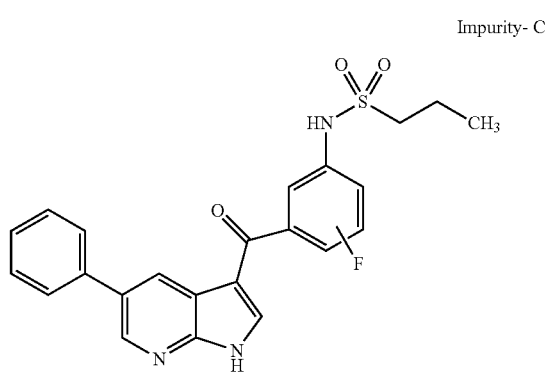

Impurity- D

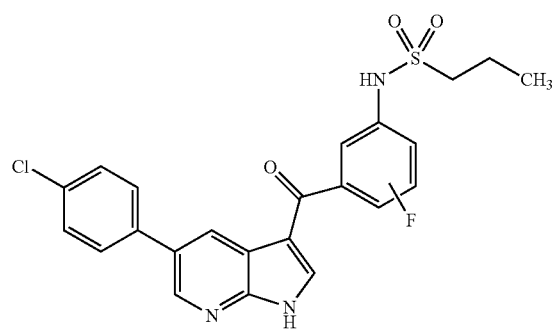

Impurity- E (Compound of Formula B)

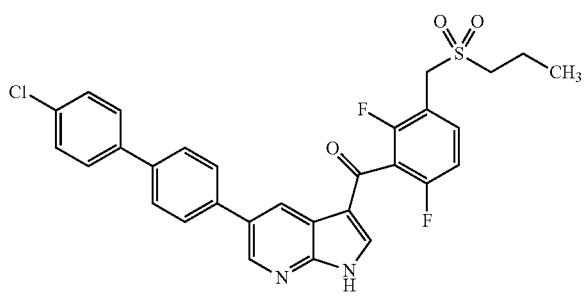

In yet another embodiment of the invention related to a process for the preparation of substantially pure Vemurafenib trifluomethane sulfonic acid salt, wherein substantially pure Vemurafenib contains the process related impurities A, B, C, D and E collectively below 0.3% and meeting the ICH guidelines.

Impurity- A

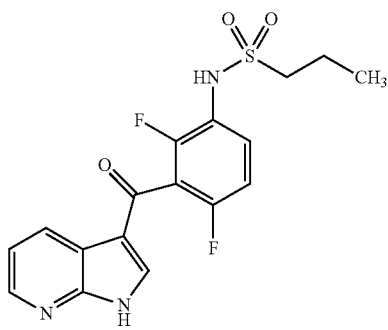

Impurity- E (Compound of Formula B)

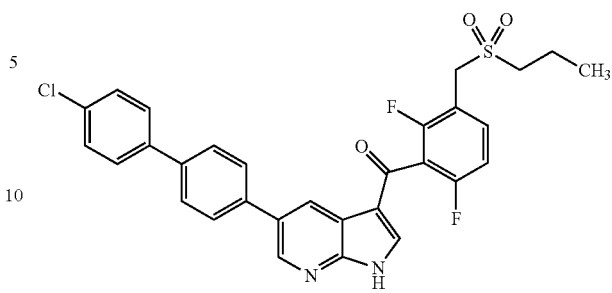

Impurity- B

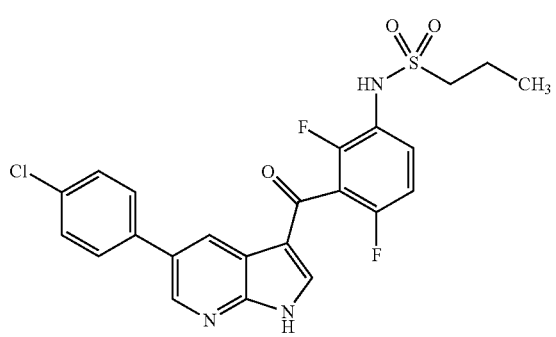 [SMILES: CCCS(=O)(=O)Nc1ccc(F)c(C(O)c2c[nH]c3ncc(-c4ccc(Cl)cc4)cc23)c1F]

Impurity- C

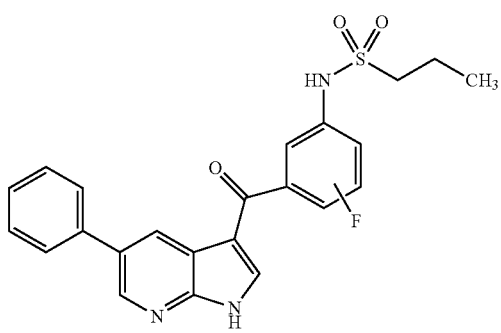

Impurity- D

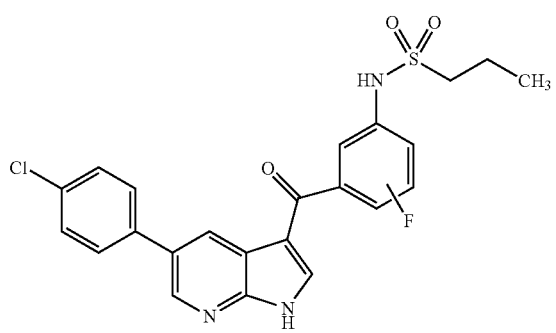

In an another embodiment of the invention related to a process for the preparation of substantially pure Vemurafenib, wherein substantially pure Vemurafenib contains the process related impurities A, B, C, D and E collectively below 0.2% and meeting the ICH guidelines.

In an another embodiment of the invention related to a process for the preparation of substantially pure Vemurafenib, wherein substantially pure Venmurafenib contains the process related impurities A, B, C, D and E collectively below 0.1% and meeting the ICH guidelines.

Another embodiment of the present invention related to a process for the preparation of substantially pure Vemurafenib comprising the steps of—
 a) treating Vemurafenib or Vemurafenib hydrate or solvate or salt with an alkaline solution; and
 b) optionally, reacting Vemurafenib or Vemurafenib hydrate or solvate or salt with an acid forming salt to form the corresponding salt, followed by basification with an alkaline solution to obtain substantially pure Vemurafenib(I)

The present invention relates to a process for the preparation of substantially pure Vemurafenib comprising the steps of reacting Vemurafenib or Vemurafenib hydrate or solvate or salt with an acid forming salt selected from organic acid such as acetic acid, oxalicacid, p-toluene sulfonic acid, dichloro acetic acid, Lactic acid, formic acid, citric acid, Uric acid, Malic acid, Maleic acid, glucornic acid; or inorganic acid such as Hydrochloric acid, Hydrobromic acid, Hydrofluoric acid, Sulphuric acid, Boric acid, Chloric acid, Chromic acid, trifluoromethane sulfonic acid, methane sulfonic acid to from the corresponding salt. The obtained salt is treated with an alkaline solution, wherein alkaline solution used is prepared using a base selected from organic base such as triethylamine, methylamine, pyridine, imidazole, benzimidazole; or inorganic base selected from carbonates such as sodium carbonate, potassium carbonate, calcium carbonate, ammonium carbonate; hydroxides such as sodium hydroxide, potassium hydroxide, calcium hydroxide, ammonium hydroxide, barium hydroxide, magnesium hydroxide, lithium hydroxide, zinc hydroxide; bicarbonates such as sodium bicarbonate, potassium bicarbonate, ammonium bicarbonate, calcium bicarbonate, magnesium bicarbonate; in a solvent selected from organic solvent or water; to obtain substantially pure Vemurafenib(I). If required, optionally repeat again the acidification followed by basification to obtained desired purity, wherein the Vemurafenib obtained as per the present invention is having a purity of greater than 99.5%.

Another embodiment of the present invention relates to substantially pure Vemurafenib having a purity of greater than 99.5%. In another particular embodiment of the present invention relates to substantially pure Vemurafenib having a purity of greater than 99.6%. In another particular embodiment of the present invention relates to substantially pure Vemurafenib having a purity of greater than 99.7%. In another particular embodiment of the present invention relates to substantially pure Vemurafenib having a purity of greater than 99.8%. In another particular embodiment of the present invention relates to substantially pure Vemurafenib having a purity of greater than 99.9%.

Another embodiment of the present invention relates to substantially pure Vemurafenib having a purity of greater than 99.5%, wherein substantially pure Vemurafenib is having an impurity profile meeting the ICH guidelines.

Another embodiment of the present invention relates to substantially pure Vemurafenib having a purity of greater than 99.5%, wherein substantially pure Vemurafenib contains the process related impurities A, B, C, D and E collectively below 0.3% area percentage by HPLC and meeting the ICH guidelines.

Another embodiment of the present invention relates to substantially pure Vemurafenib trifluoromethane sulfonic acid salt having a purity of greater than 99.5%, wherein substantially pure Vemurafenib contains the process related impurities A, B, C, D and E collectively below 0.3% area percentage by HPLC and meeting the ICH guidelines.

The process related impurities that appear in the impurity profile of the propane-1-sulfonic acid-{3-[5-(4-chlorophenyl)-1H-pyrrolo[2,3-b]pyridine-3-carbonyl]-2,4-difluoro-phenyl}-amide or Vemurafenib (I) may be substantially removed by the process of the present invention resulting in the formation of substantially pure propane-1-sulfonic acid-{3-[5-(4-chlorophenyl)-1H-pyrrolo[2,3-b]pyridine-3-carbonyl]-2,4-difluoro-phenyl}-amide or Vemurafenib (I), which meets the ICH guidelines.

The merit of the process according to the present invention resides in that product isolated after drying is stable and having a purity of greater than 99.5% purity by HPLC, which was not disclosed in any of the prior-art. The product obtained as per the present invention is highly pure than the any of the prior-art products obtained. Still now no-publication discloses a purity of greater than 99.5%. Even, the innovator product "Vemurafenib" also listed in Drugs@FDA that the "impurities are specified at levels exceeding this applicable qualification threshold because they have been detected in DS batches in amounts that exceeded the qualification threshold."

Another significant merit of the present invention lies in the solubility of Vemurafenib. The product obtained as per the present invention is highly soluble in water than the any of the prior-art products obtained. Till now no-publication discloses solubility of Vemurafenib greater than 0.001 mg/ml. Even, under the innovator product "Vemurafenib" described in scientific discussion of Zelboraf® discloses "Its solubility in water is very low (<0.0001 mg/ml) and it is not appreciably soluble in many common organic solvents either."

Solubility is one of the important parameters to achieve desired concentration of drug in systemic circulation for achieving required pharmacological response. Poorly water soluble drugs often require high doses in order to reach therapeutic plasma concentrations after oral administration. Low aqueous solubility is the major problem encountered with formulation development of new chemical entities as well as generic formulation development. Most of the drugs are either weakly acidic or weakly basic having poor aqueous solubility. The improvement of drug solubility thereby its oral bio-availability remains one of the most challenging aspects of drug development process especially for oral-drug delivery system. The poor solubility and low dissolution rate of poorly water soluble drugs in the aqueous gastrointestinal fluids often cause insufficient bioavailability. The enhancement of inherent solubility of Vemurafenib plays a major role for enhancement of drug dissolution rate in solid oral dosage forms.

According to European assessment report of Zelboraf® "Vemurafenib is a Class IV substance (low solubility and permeability), using the criteria described in the Biopharmaceutics Classification System. The drug substance, vemurafenib, is a new chemical entity. It is manufactured as the amorphous form and processed with hydroxypropyl methylcellulose acetate succinate (HPMC-AS) in a ratio of 3:7 (w:w). This is performed in order to keep the active moiety as the desired amorphous modification so as to achieve enhanced dissolution of the substance."

From above it is adequately clear that Vemurafenib is a low soluble and low permeable. As per EMEA it is clear that crystalline Vemurafenib is not stable and has been converted into amorphous substance by co-precipitation with HPMC-AS. Further, as per the EMEA "When processed with HPMC-AS, Vemurafenib becomes an amorphous white to almost white powder which is slightly hygroscopic"

In view of above, the present inventors now developed a crystalline Vemurafenib having an enhanced solubility especially in aqueous medium, and Vemurafenib is also stable, having purity of greater than 99.5% which meets ICH guidelines.

The present invention also relates to a process for the preparation of Vemurafenib, which is substantially pure having a purity of greater 99.5% and meeting the ICH guidelines, by limiting the content of each impurity less than 0.15%. Further, the Vemurafenib obtained as per the present process is found devoid of any other process related impurities and is adequately stable to handle and store for longer time (at least up to more than 6 months) without any significant or measurable change in its morphology and physicochemical characteristics.

The Vemurafenib produced by following the process described in the present invention was further analyzed by powder X-ray diffraction, which is similar to the XRPD pattern characterized similar to as shown in FIG. 1, which is substantially pure Vemurafenib contains the process related impurities A, B, C, D and E collectively below 0.3% and meeting the ICH guidelines and having a purity of greater than 99.5%.

|  | Marketed form/Prior reported forms | As per the present invention |
| --- | --- | --- |
| Impurity Level | A single impurity was identified during the course of the review as being above the level for qualification. | Vemurafenib contains process related impurities A, B, C, D and E collectively below 0.3% and meeting the ICH guidelines and having a purity of greater than 99.5%. |
| PXRD | Form-II (As disclosed in EMEA) | Form-SVM |
| Melting Point | 271° C. | 272.17° C. |
| Solubility in water | <0.0001 mg/ml | >0.001 mg/ml |

Various processes and salts are disclosed in the literature for the formation of Vemurafenib salt. However, no salt enhances the purity of Vemurafenib formed. The present inventors also tried for the formation of so many salts.

Despite of that Vemurafenib Trifluoromethane sulfonic acid (Triflate salt) enhances the purity of Vemurafenib salt, which up on transferred to the pure form of Vemurafenib results in the formation of substantially pure Vemurafenib, which is free of process related impurities and meeting the ICH guidelines.

Drying may be also be performed by any conventional process not limited to spray drying or distillation to remove the solvent. Drying may be performed under reduced pressure conditions also. Reduced pressure conditions may be suitably utilized by person skilled in the art in order to obtain the dried material. The drying may be performed at a temperature ranging from 50-85° C. for a time ranging from 5 to 10 hours depending upon the physical attributes of the end product obtained i.e. Pure Vemurafenib. propane-1-sulfonic acid-{3-[5-(4-chlorophenyl)-1H-pyrrolo[2,3-b]pyridine-3-carbonyl]-2,4-difluoro-phenyl}-amide(I) or Vemurafenib obtained according to the present invention is having purity greater than 99.5%.

In another embodiment of the present invention relates to a substantially pure crystalline Vemurafenib having purity of greater than 99.5% is characterized by x-ray powder diffraction (XRPD) pattern having
a) characteristic peaks at 9.3, 15.0, 19.2, 19.8 and 24.4°2θ±0.2°2θ; and
b) solubility of greater than 0.001 mg/ml in water.

In another embodiment of the present invention relates to a substantially pure crystalline Vemurafenib trifluoro methane sulfonic acid salt having purity greater than 99.5% is characterized by x-ray powder diffraction (XRPD) pattern having characteristic peaks at 6.9, 13.9, 17.2, 18.3, 18.7, 19.0, 21.0, 22.3, 24.0, 24.2, 25.0, 25.5 and 30.3±0.2°2θ and solubility of ≥0.001 mg/ml in water.

The obtained crystalline pure propane-1-sulfonic acid-{3-[5-(4-chlorophenyl)-1H-pyrrolo[2,3-b]pyridine-3-carbonyl]-2,4-difluoro-phenyl}-amide or Vemurafenib(I) having purity greater than 99.5% and contains the process related impurities A, B, C, D and E collectively below 0.3% and meeting the ICH guidelines.

The process related impurities that appear in the impurity profile of the propane-1-sulfonic acid-{3-[5-(4-chlorophenyl)-1H-pyrrolo[2,3-b]pyridine-3-carbonyl]-2,4-difluoro-phenyl}-amide or Vemurafenib (I) may be substantially removed by the process of the present invention resulting in the formation of highly pure crystalline material. The process of the preparation of propane-1-sulfonic acid-{3-[5-(4-chlorophenyl)-1H-pyrrolo[2,3-b] pyridine-3-carbonyl]-2,4-difluoro-phenyl}-amide or Vemurafenib (1) used in the present invention is as summarized below in Scheme-I:

Scheme-I: Process of the preparation of Vemurafenib

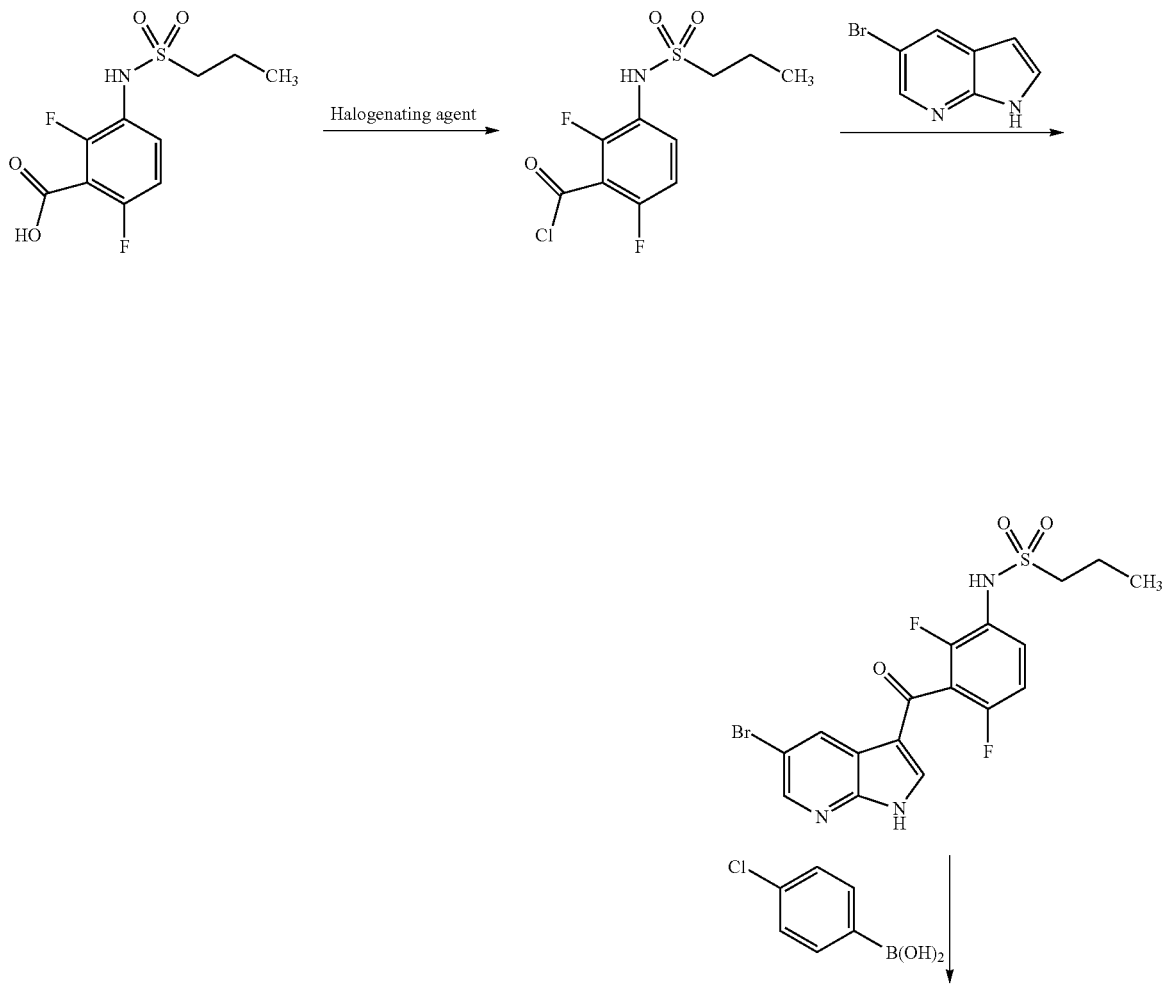

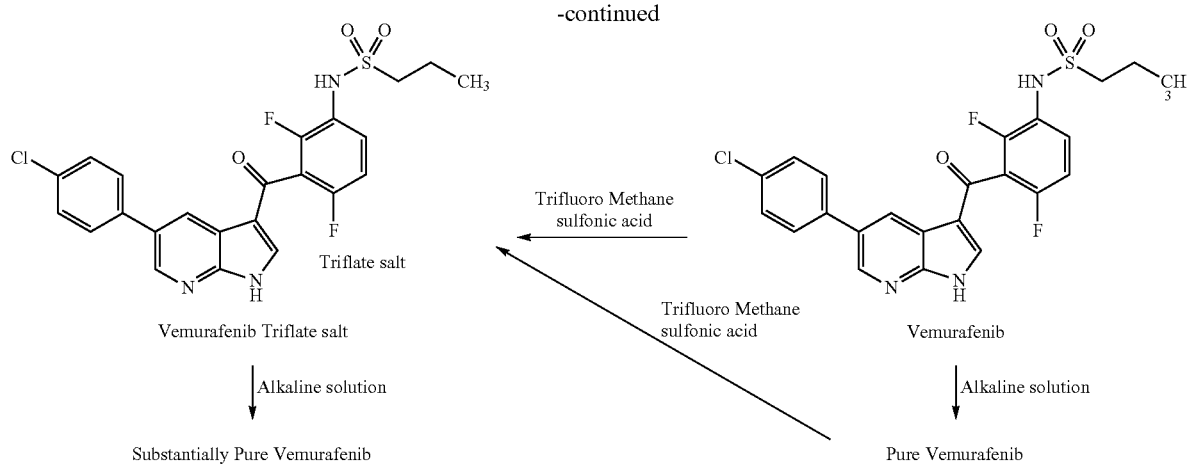

In another embodiment of the present invention the substantially pure Vemurafenib or its acid addition salt obtained by the processes of the present application may be taken as such in crystalline form for manufacture of solid dosage forms like tablets, capsules and/or for manufacture of oral liquids.

In another embodiment of the present invention the substantially pure Vemurafenib or its acid addition salt obtained by the processes of the present application may be manufactured as the amorphous form by processing with polymers like hydroxypropyl methylcellulose acetate succinate (HPMC-AS).

In another embodiment, the substantially pure Vemurafenib or its acid addition salt obtained by the processes of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

In one embodiment of the present invention, it also includes premix comprising one or more pharmaceutically acceptable excipients in the range of 1 to 50% w/w with the substantially pure Vemurafenib or its acid addition salt, while retaining the crystalline nature of the premix.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising substantially pure Vemurafenib or its acid addition salt obtained as per the present application process—include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from substantially pure Vemurafenib or its acid addition salt of the present application may also comprise to include the pharmaceutically acceptable carrier used for the preparation of solid dispersion, wherever utilized in the desired dosage form preparation.

The following examples illustrate the nature of the invention and are provided for illustrative purposes only and should not be construed to limit the scope of the invention.

EXAMPLES

Example 1

Preparation of 3-(Propane-1-sulfonylamino)-benzoyl chloride (III)

Charge 2, 6-difluoro-3-(((propan-1-yl) sulphonyl) amino) benzoic acid (5 gm, 0.018 mol) was charged in to a reaction flask at 25-30° C. containing Toluene (25 ml) under nitrogen atmosphere. Reaction mass was cooled to 10-15° C. Thionyl chloride (15 ml, 0.077 mol) was added drop wise to mass at 10-15° C. and stirred for 15 min. Reaction mass allowed to warm 25-30° C. and stirred for 30 min. Heated the reaction mass to 105-110° C. and stirred for 4 hrs. Reaction mass cooled to 55-60° C. and organic volatiles distilled off completely to get semisolid residue and as such used in-situ for next stage.

Example 2

Preparation of propane-1-sulfonic acid-{3-[5-1H-pyrrolo[2,3-b]pyridine-3-carbonyl]-phenyl}-amide (IV)

Charge aluminum chloride (12.5 gm, 0.093 moles) was charged in to a reaction flask at 0-5° C. containing dichloromethane (65 ml) and stirred for 10-15 min. Prepared solution of 5-bromo-1H-pyrrolo[2,3-b]pyridine (2.5 gm, 0.012 moles) in dichloromethane (50 ml) was slowly added in to reaction mass at 0-5° C. over a period of 45 min to 1 hr. Reaction mass allowed to warm 5-10° C. Solution of 3-(Propane-1-sulfonylamino)-benzoyl chloride (in dichloromethane (50 ml)) was added to reaction mass over a period of 45 min to 1 hr at 5-10° C. Reaction mass stirred at 20-25° C. for 14 hrs to complete reaction. Reaction mass quenched in chilled water (500 ml) slowly at below 15° C. and stirred for 30 min. The precipitated product was filtered and washed the wet cake with water. Wet cake was dissolved in mixture of ethyl acetate (100 ml) and methanol (20 ml) solvent and washed with water for twice. Organic layer was dried over sodium sulphate and distilled off solvent completely to get residue. To the obtained residue hexane was added and stirred for 45 min. Precipitated product was filtered on Buchner funnel, washed with hexane and dried at 50-55° C. to yield the title product.

Yield: 3.7 g; Chromatographic Purity (By HPLC): 99.28%

Example 3

Preparation of Vemurafenib

Propane-1-sulfonic acid-{3-[5-1H-pyrrolo[2,3-b]pyridine-3-carbonyl]-phenyl}-amide (5 gm, 0.011 mol), 4-Chlorophenylboronic acid (2.44 grm, 0.015 mol), DMF (100 ml) was charged in to a clean and dry RBF at 20-25° C. under nitrogen atmosphere. Prepared one molar aqueous potassium carbonate solution (150 ml) was added to reaction mass. Bis (triphenylphosphine)palladium (II) dichloride (1.24 grm, 0.001 mol) was added to mass under nitrogen atmosphere at 25-30° C. and stirred for 10-20 min at same temperature under nitrogen atmosphere. Reaction mass heated to 95-105° C. and stirred at same temperature for 6 hr till reaction completion. After complete conversion, reaction mass was cooled to 25-30° C., filtered through high flow bed and washed with water. Total collective aqueous layer extracted twice with ethyl acetate. Total combined organic layer was washed twice with water and dried over sodium sulfate. Organic layer was distilled off under vacuum collectively at 40-45° C. to get residue. Ethyl acetate charged to residue and stirred for 45-60 min at 20-30° C. Precipitated product filtered on Buchner funnel, washed with ethyl acetate and dried at 40-45° C. under vacuum for 4 hrs to yield the titled product Yield: 3.5 g; Chromatographic Purity (By HPLC): 95.52%

Example 4

Purification of Vemurafenib Using Base

Crude Vemurafenib (60 gm, 0.12 moles) was charged in to a reaction vessel containing 5% aqueous NaOH solution (1200 ml) and stirred at 45-50° C. for 30 min to get clear solution. To the reaction mass mixture of ethyl acetate and toluene (300 ml; in the ratio of 3:7) was added at 25-30° C., stirred the contents for 10 min and separated the aqueous layer. To the Aqueous layer mixture (300 ml) of ethyl acetate and toluene was added under stirring and maintained stirring at 25-30° C. for 30-60 min to get product precipitation. Precipitated product was filtered on Buchner funnel and washed with water to get wet cake material. The wet cake material was slurred in 5% ammonium chloride solution (600 ml) and filter on Buchner funnel, washed with water and suck dried for 30 min. The wet cake material unloaded and dried under vacuum at 70-75° C. for 6 hrs to yield pure title product Yield: 57.0 g; Chromatographic Purity (By HPLC): 99.47%

Example 5

Purification of Vemurafenib Using Saltification and Desaltification Method

Trifluoromethanesulphonic acid (22.95, 0.15 mol) was charged slowly in to a reaction flask containing cooled solution of Vemurafenib (50 gm, 0.10 mol) and acetone (450 ml) at 0-5° C. The reaction mass was stirred at 0-5° C. for 3 hrs to 3 hrs 30 min. The precipitated product was filtered, washed the wet cake with ethyl acetate and suck dried for 30 min. The wet cake was charged into a reaction flask containing DMSO (250 ml) and stirred for 10 min to get clear solution. Optionally, reaction mass filtered through celite bed to remove undissolved particles. Obtained reaction mass was charged in to potassium carbonate solution (0.5% aqueous potassium carbonate solution (3500 ml) freshly prepared) slowly at 25-30° C. over a period of 60-90 min. Reaction mass was stirred for 2 hrs, cooled to 0-5° C. and maintained under stirring for 1 hr. Precipitated product was filtered on Buchner funnel, washed with water followed by methanol and dried under vacuum at 70-75° C. for 6 hrs to yield substantially pure title product Yield: 35 g; Chromatographic Purity (By HPLC): 99.83%;

Moisture content: 0.4%; XRPD was found resemble to FIG. 1.

Impurity A: 0.03% (By HPLC); Impurity B: 0.06% (By HPLC);

Impurity C: 0.05% (By HPLC); Impurity D: 0.01% (By HPLC)

Example 6

Preparation of VemurafenibTrifluoro Methane Sulfonic Acid Salt (VI)

Trifluoro methane sulphonic acid (1.52 gm, 0.010 mol) was charged in to a reaction flask containing a cooled solution of Vemurafenib obtained as per example −3 (3 gm, 0.006 mol) and acetone (42 ml) at 0-5° C., over a period of 10 min to 15 min. The reaction mass was cooled to 0-5° C. and stirred for 60 min to 90 min, precipitated product was filtered, washed wet cake with acetone and dried under vacuum at 50-55° C. for 2 hrs to yield the title product.

Yield: 3.0 g

Chromatographic Purity (By HPLC): 99.6%

Impurity A: 0.01% (By HPLC); Impurity B: Not detected (By HPLC);

Impurity C: 0.06% (By HPLC); Impurity D: 0.08% (By HPLC)

Example 7

Preparation of Vemurafenib

Vemurafenib triflic acid salt obtained as per example −6 (2.5 gm, 0.0039 mol) was charged in to a reaction flask containing dimethyl formamide (7.5 ml) at 25-30° C. and stirred for 30 min to get clear solution. Prepared 1% aqueous potassium carbonate solution (340 ml) was added slowly to reaction mass at 25-30° C. over a period of 15-30 min. Reaction mass stirred for 2 hrs at 25-30° C., cooled to 0-5° C. and maintained under stirring for 30 min. Precipitated product was filtered on Buchner funnel, washed with water followed by acetone and dried under vacuum at 60-65° C. for 5 hrs to yield substantially pure title product Yield: 1.6 g;

Chromatographic Purity (By HPLC): 99.79%; XRPD was found resemble to FIG. 1.

While the foregoing pages provide a detailed description of the preferred embodiments of the invention, it is to be understood that the summary, description and examples are illustrative only of the core of the invention and non-limiting. Furthermore, as many changes can be made to the invention without departing from the scope of the invention, it is intended that all material contained herein be interpreted as illustrative of the invention and not in a limiting sense.

The invention claimed is:

1. A substantially pure crystalline Vemurafenib having a purity of greater than 99.5% is characterized by x-ray powder diffraction (XRPD) pattern having
   a) characteristic peaks at 9.3, 15.0, 19.2, 19.8 and 24.4°2θ±0.2°2θ; and
   b) solubility of greater than 0.001 mg/ml in water.

2. A substantially pure Vemurafenib having a purity of greater than 99.5% according to claim 1, wherein substantially pure Vemurafenib having water solubility of greater than 0.001 mg/ml.

3. A substantially pure Vemurafenib having a purity of greater than 99.5% according to claim 1, wherein process related impurities A, B, C, D and E are collectively below 0.3% and meeting the ICH.

* * * * *